(12) United States Patent
Brown

(10) Patent No.: US 6,344,448 B1
(45) Date of Patent: Feb. 5, 2002

(54) COMPOSITION FOR THE TREATMENT OF HAIR LOSS

(75) Inventor: Sandra Brown, Southfield, MI (US)

(73) Assignee: STB Family Limited Partnership, Southfield, MI (US)

( * ) Notice: Subject to any disclaimer, the term of this patent is extended or adjusted under 35 U.S.C. 154(b) by 0 days.

(21) Appl. No.: 08/273,423

(22) Filed: Jul. 11, 1994

Related U.S. Application Data

(63) Continuation-in-part of application No. 08/207,821, filed on Mar. 7, 1994, now abandoned, and a continuation-in-part of application No. 07/943,853, filed on Sep. 11, 1992, now abandoned.

(51) Int. Cl.$^7$ ........................ A61K 31/56; A01N 45/00; A01N 37/00
(52) U.S. Cl. ........................ 514/179; 514/171; 514/180; 514/559
(58) Field of Search ................................ 514/179, 171, 514/180, 559

(56) References Cited

U.S. PATENT DOCUMENTS

| | | | |
|---|---|---|---|
| 3,729,568 A | 4/1973 | Kligman | 424/318 |
| 4,889,847 A | 12/1989 | Kligman et al. | 514/171 |
| 5,019,569 A | 5/1991 | Kligman et al. | 514/171 |
| 5,026,691 A * | 6/1991 | Kligman | 514/171 |

FOREIGN PATENT DOCUMENTS

AU 35854/93 9/1993

OTHER PUBLICATIONS

Topical Tretinoin For Hair Growth Promotion, Gail S. Bazzano, PhD, Nia Tereszkis, MD, & Wesley Galen, MD, Journal of the American Academy of Dermatology, No. 4, Part 2, Dec., 1986, pp. 880–883.

Topical All–Trans–Retinoic Acid Prevents Corticosteroid–Induced Skin Atrophy Without Abrogating The Anti–Inflammatory Effect, Robert H. Lesnik, MD, et al., Journal of the American Academy of Dermatology, vol. 21, No. 2, Part 1, Aug., 1989, pp. 186–190.

Immune Privilege in Hair Growth, Gillian E. Westgate, et al., The Journal of Investigative Dermatology, pp. 417–419, 1991.

NX3 Nutrient Booster Intensive Treatment for Thinning Hair, (Product Box & Flyer), Nioxin Research Laboratories, Inc., Atlanta, Georgia 1991.

Rogaine, Topical Solution, (Flyer), Upjohn Dermatology Division, The Upjohn Company, Kalamazoo, Michigan, May, 1993.

Human Anatomy and Physiology, John W. Hole, Jr., William C. Brown, Publishers, pp. 163–165, 904–906, 1992.

Pathophysiology, Clinical Concepts of Disease Processes, Third Edition Price & Wilson, McGraw–Hill Book Company, pp. 1006–1009, 1986.

Effect of Retinoids on Follicular Cells, Gail Bazzano, Nia Terezakis, Hala Attia, Alicia Bazzano, Robin Dover, David Fenton, Nikki Mandir, Leonardo Celleno, Maria Tamburro, Stefano Jaconi. The Journal of Investigative Dermatology, vol. 101, No. 1, Supplement, Jul. 1993, 138S–142S.

Changes in Populations of HLA–DR+CD3+Cells and CD57–CD16+ Cells in Alopecia Areata After Corticosteroid Therapy. R. Imai, K. Takamori, H. Ogawa, 1994, Dermatology 188(2): 103–7.

The Developing Organ of Corti Contains Retinoic Acid and Forms supenumerary Hair Cells in Response to Exogenous Retinoic Acid in Culture. Matthew W. Kelley, Xiao–Mei Xu, Michael A. Wagner, Mark E. Warchol, Jeffrey T. Corwin, 1993, Development 119: 1041–1053.

Retinoic Acid Stimulates Regeneration of Mammalian Auditory Hair Cells. Philippe P. Lefebvre, Brigitte Malgrange, Hinrich Staecker, Gustave Moonen, Thomas R. Van De Water, 1993, Science 260: 692–695.

The Cutaneous Safety of Topical Tretinoin. Christopher M. Papa, 1975, Acta Dermatovener 74 Suppl: 128–132.

Dermal Papilla Cells from Human Hiar Follicles Express mRNA for Retinoic Acid Receptors in Culture. Valerie A. Randall, M. Julie Thornton, Christopher P.F. Redfern, 1991, Ann NY Acade Sci. 642: 457.

Topical Retinoic Acid Does Not Alter the Vasconstrictive Properties of Topical Corticosteroids in Humans. C. Schmied, Saurat J.H., 1991, Dermatologica 182: 107–111.

Retinoic Acid and Mouse Skin Morphogenesis. I. Expression Pattern of Retinoic Acid Recepton Genes During Hair Vibrissa Follicle, Plantar, and Nasal Gland Development. Jean P. Viallet and Danielle Dhouailly, 1994, J. Invest Dermator. 103: 116–121.

Alopecia: Evaluation and Management. Elise A. Olsen, MD, Sep. 1989, Primary Care, vol. 16, No. 3, 765–787.

Immune Privilege in Hair Growth. Gillian E. Westgate, Robert I. Craggs and Walter T. Gibson, 1991, Journal Investigative Dermatology, 97:417–420.

* cited by examiner

*Primary Examiner*—Minna Moezie
*Assistant Examiner*—S. Jiang
(74) *Attorney, Agent, or Firm*—Gifford, Krass, Groh, Sprinkle, Anderson & Citkowski, P.C.

(57) ABSTRACT

A method and compound having betamethasone dipropionate and all-trans-retinoic is disclosed for the treatment of hair loss. The method also includes identifying any underlying conditions causing hair loss and administration of a salve of betamethasone dipropionate and all-trans-retinoic acid to the affected areas.

9 Claims, 1 Drawing Sheet

COMPOSITION FOR THE TREATMENT OF HAIR LOSS

"This is a continuation-in-part of application Ser. No. 07/943,853 filed on Sep. 11, 1992 now abandoned which is a continuation-in-part of Ser. No. 08/207,821 filed on Mar. 7, 1994 now abandoned.

BACKGROUND OF THE INVENTION

I. Field of the Invention

The present invention relates to a compound and method of treatment for hair loss, and more particularly, to a compound and method using a compound having all-trans-retinoic acid and betamethasone dipropionate.

II. Description of the Prior Art

Restoration of human hair has been attempted for centuries. In many cases, hair loss is merely covered by wigs or toupees. Many medical treatments have been attempted over the years; however, up until now, no treatment has been found which satisfactorily stimulates hair growth for a wide variety of cases, including alopecia.

Each hair extends from a tube-like depression called a hair follicle. The hair follicle extends from the surface of the skin into the dermis and may pass into the subcutaneous layer. At the base of the follicle is a group of epidermal cells which receive nourishment from blood vessels that occur in a projection of connective tissue at the base of the follicle.

As the epidermal cells divide and grow, older cells are pushed toward the surface. The cells that move upward and away from the nutrient supply become keratinized and die. Thus, hair is dead keratin, just like scale, and is formed at a predetermined rate.

The normal rate of growth of hair is 1 cm per month. Each hair follicle goes through a cycle of a growth stage (anagen hair), and an involution or resting stage (telogen hair). The anagen stage lasts about three years, while the telogen stage lasts only about three months. Once the hair follicle reaches the end of the telogen stage, the hair falls out. Eventually, the hair follicle produces a new growing hair.

The cycle of hair activity for hair follicles is independent for each hair follicle. However, when the hair follicles fail to regenerate hair, baldness results.

Many causes of hair loss are known. Exposure to chemotherapy, X-ray therapy, exposure to toxic chemicals, and topical chemicals on the scalp can cause anagen hair loss. Hormonal imbalances, stress, nutritional deficiency, and usage of many drugs can cause telogen effluvium. The cause of alopecia areata is unknown, and male/female andro-genetic alopecia is caused by genetics. There are numerous other causes of hair loss, as well.

It is known that the hair follicle is an immune-privileged organ, and it has been postulated that hair growth may be regulated by the immune system (Frusgate et al., *Journal of Investigative Dermatology*, 97: 417–420, 1991). Thus, in order to restore hair, it is necessary to treat any underlying causes of the hair loss, such as disease, stress, hormonal imbalance, or nutritional deficiency. It is known, as disclosed by Olson (Alopecia Evaluation, *Primary Care* 1989: 16 (3), p. 765–787), to treat hair loss by making an evaluation of the patient, including patient history, physical exam, and lab studies, treating any treatable underlying causes of hair loss, and treating alopecia with topical minoxidil and antiandrogens. However, treatment with minoxidil has many undesirable side effects and hair growth, if it occurs, takes place only as long as the minoxidil is being used. Thus, in order to restore hair growth, it is desirable to overcome the causes of alopecia and permit hair follicles to grow hair without continuous stimulation, such as by minoxidil.

It is known to use various commercial shampoo preparations to strengthen the hair. These shampoos typically include protein and affect only dead keratin, not the hair follicle, and therefore cannot prevent hair loss.

SUMMARY OF THE INVENTION

Applicant's method and compound for hair restoration produces hair growth in all cases of hair loss arising from all of the previously-recited causes for this condition. The rate of hair growth is greater than previously known methods and compounds. The method includes first identifying the causes of the patient's hair loss. The identification step includes a complete patient history to identify dietary problems, stress, genetic factors, and drug usage. Additionally, the patient is given a physical exam for identifying hormonal imbalances and disease. Then, an external examination of the scalp and condition of the hair is made.

After the identification step, a diagnosis is made. Following the diagnosis, an application of betamethasone dipropionate and all-trans-retinoic acid is made to the patient. The betamethasone dipropionate and all-trans-retinoic acid are administered together in a compound applied topically to the scalp. The compound and method have been found to effectively restore hair growth even after discontinuance of use of the compound.

DETAILED DESCRIPTION OF THE PREFERRED EMBODIMENTS

Figure 1:
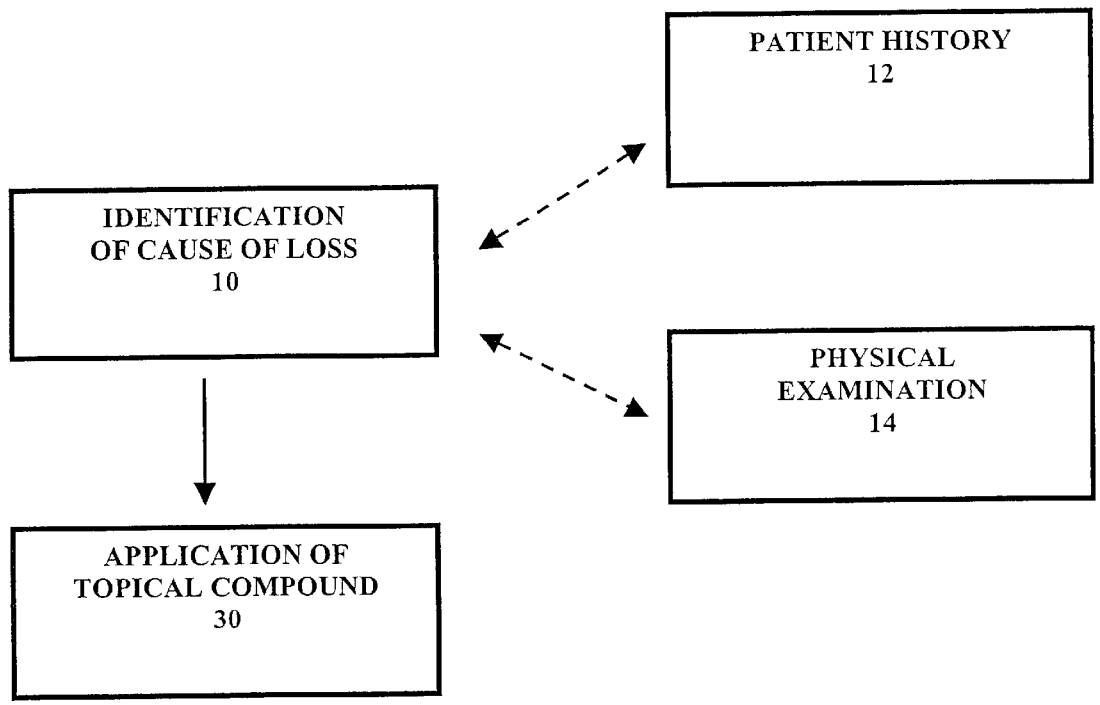
FIG. 1 is a block diagram of the method of treatment according to the invention.

Disclosed herein is a method of promoting hair growth using corticosteroids in combination with Vitamin A derivatives. As best shown in FIG. 1, Applicant's method includes the steps of identifying the underlying cause of hair loss 10; conducting a physical examination 14; and administering a compound of all-trans-retinoic acid and betamethasone dipropionate to the scalp of the patient 30.

As stated above, there are many known causes for hair loss. These causes include genetic disorder, hormonal imbalance, nutritional deficiency, and stress. Additionally, many external occurrences may result in hair loss, such as chemotherapy, toxic exposure, drugs, and X-ray therapy. Thus, the identification step 10 includes making a complete patient history 12. The patient history includes obtaining information regarding drugs, major illnesses, weight loss or gain, major stress occurrences, as well as family background for genetic evaluation.

The identification step 10 also includes making an examination of the scalp and hair and an examination of the patient's physical condition 14. The physical examination may include the taking of blood pressure readings, a thyroid exam, and lab studies to determine whether any physiological imbalances are causing the hair loss.

After evaluating the patient's condition, a diagnosis may be made as to the causes of hair loss. After the diagnosis, the patient is treated with a compound containing a corticosteroid in combination with a Vitamin A derivative. As set forth below, the preferred embodiment is in the form of a topical gel containing a suspension of betamethasone dipropionate as the preferred corticosteroid, and all-trans-retinoic acid as the preferred Vitamin A derivative.

Betamethasone dipropionate is a steroid and has a tendency to thin the dermis. All-trans-retinoic acid is also administered in combination with betamethasone dipropionate. However, one of the well-known side effects of all-trans-retinoic acid is that it acts to thicken the skin. Thus, when used in combination with each other, the negative side effects of betamethasone dipropionate and all-trans-retinoic acid act to cancel each other out while synergistically producing a large amount of hair. In the preferred embodiment, the betamethasone dipropionate and all-trans-retinoic acid are applied in combination with each other as a topical preparation in the form of a gel. The ratio of betamethasone dipropionate to all-trans-retinoic acid ranges from 1:1 to 15:1, with 4:1 being the preferred ratio.

Initially, the user should apply the salve of the present invention once a day. Applicant's experimental data has disclosed that by doubling the amount of betamethasone dipropionate while leaving unchanged the amount of all-trans-retinoic acid, (i.e., from a 2:1 to a 4:1 ratio) a significant increase in the efficacy of the salve is achieved. The salve of the present invention may be provided in the form of a gel, an ointment, a cream, or a liquid.

EXAMPLE 1

In the preferred embodiment of the compound, a topical gel was formed having betamethasone dipropionate and all-trans-retinoic acid as main active ingredients. The gel is made in 4800 g batches. 600 mg of pure all-trans-retinoic acid powder, 1200 mg of pure betamethasone dipropionate powder, 2400 g of 0.05% betamethasone dipropionate lotion (available from Lemmon Laboratory in Sellersville, Pa.) and 2400 g of Liqua-Gel™ (available from Paddock Laboratory in Minneapolis, Minn.) were weighed out on an analytical balance. The all-trans-retinoic acid powder and the betamethasone dipropionate powder were ground together with a mortar-and-pestle. The betamethasone dipropionate lotion and the Liqua-Gel were then added to the ground powders in order to put them into suspension. The resulting compound contains 0.05% by weight betamethasone dipropionate and 0.0125% by weight all-trans-retinoic acid, for a corticosteroid-to-Vitamin A derivative ratio of 4:1.

The gel was applied to the scalp of a patient diagnosed with male-pattern baldness. The patient had scar tissue on the scalp resulting from scalp reduction surgery. The gel was applied in a thin layer to the patient's scalp once per day. Visible hair re-growth around the periphery of the hairless area was evident after one month. After four months, virtually all of the previous hairless area was covered with hair, with new hair growth covering through scar tissue.

EXAMPLE 2

The same protocol as outlined in Example 1 was followed, except the resulting compound contained 0.025% by weight betamethasone dipropionate and 0.0125% by weight all-trans-retinoic acid, or a corticosteroid-to-Vitamin A derivative ratio of 2:1.

This compound was found to be about half as effective on patients suffering from hair loss, as compared to the compound containing a 4:1 ratio of betamethasone dipropionate to all-trans-retinoic acid, which was found to be 100% effective on patients suffering from hair loss for any reason whatsoever.

In patients for which the compound containing a 2:1 ratio of betamethasone dipropionate to all-trans-retinoic acid was effective, the compound took approximately three to four times as long to show visible results of hair growth as the compound containing a 4:1 ratio. Finally, the compound containing the 2:1 ratio did not dissolve scar tissue.

The gel is applied to the affected scalp once a day. Since any excess gel will dry on the scalp and flake, the gel should be applied in as thin a coat as possible. Although it is possible to rub the gel into affected portions of the scalp, it is not necessary to do so, as it has been found that mere contact by the gel with the scalp produces desired results. Outstanding results, including hair growth within one week of applying the compound, were observed. It is believed that treatment will be successful with other proportions of the active ingredients, as well as different combinations of a corticosteroid in combination with a Vitamin A derivative.

It is believed that the corticosteroid and the Vitamin A derivative work synergistically together to cancel out the harmful side effects of each other in order to rejuvenate the hair follicles in the scalp.

It is understood, of course, that the invention is not limited to the particular embodiments described herein. For instance, it is within the contemplation of the invention to use any corticosteroid or any Vitamin A derivative, and the proportions described may be varied.

I claim:

1. A composition for the treatment of hair loss comprising effective amounts of:
   a corticosteroid,
   a Vitamin A derivative, and
   a carrier agent for said corticosteroid and said Vitamin A derivative.

2. The composition of claim 1, wherein the corticosteroid comprises betamethasone dipropionate.

3. The composition of claim 1, wherein the Vitamin A derivative comprises all-trans-retinoic acid.

4. The composition of claim 1, wherein the carrier agent is adapted to suspend said corticosteroid and said Vitamin A derivative.

5. The composition of claim 2, wherein the effective amount of betamethasone dipropionate is 0.05% by weight.

6. The composition of claim 3, wherein the effective amount of all-trans-retinoic acid is 0.0125% by weight.

7. The composition of claim 1, wherein a range of ratios of said corticosteroid to said Vitamin A derivative is between approximately 1:1 and 15:1.

8. The composition of claim 1, wherein the ratio of said corticosteroid to said Vitamin A derivative is approximately 4:1.

9. The composition of claim 8, wherein said corticosteroid comprises betamethasone dipropionate and said Vitamin A derivative comprises all-trans-retinoic acid.

* * * * *

UNITED STATES PATENT AND TRADEMARK OFFICE
CERTIFICATE OF CORRECTION

PATENT NO.     : 6,344,448 B1
DATED          : February 5, 2002
INVENTOR(S)    : Sandra Brown It is certified that error appears in the above-identified patent and that said Letters Patent is hereby corrected as shown below:

Title page,
Item [73], Assignee, insert -- The -- before "STB"
Item [56], Related U.S. Application Data, replace "and a" with -- which is a --

OTHER PUBLICATIONS, replace "vol." with -- Vol. --
Insert -- Sept. -- before "1991"
Insert -- An Approach To The Patient With Hair Loss, Elise A. Olsen, M.D. --
Replace "Hiar" with -- Hair --
Replace "Vasconstrictive" with -- vasconstrictive --

Column 1,
Line 4, delete """ before "This"
Line 4, reverse order of applications Column 3,
Line 50, replace "covering" with -- coming --

Signed and Sealed this

Twenty-fourth Day of December, 2002

JAMES E. ROGAN
*Director of the United States Patent and Trademark Office*